United States Patent [19]

Phillips

[11] Patent Number: 5,290,319
[45] Date of Patent: Mar. 1, 1994

[54] PROSTHETIC FOOT INCORPORATING ADJUSTABLE BLADDERS

[76] Inventor: Van L. Phillips, 5499 Avenida Maravillas, Rancho Sante Fe, Calif. 92067

[21] Appl. No.: 662,783

[22] Filed: Feb. 28, 1991

[51] Int. Cl.⁵ .............................................. A61F 2/66
[52] U.S. Cl. ........................................ 623/56; 623/50; 623/55
[58] Field of Search ............................ 623/27, 47–56

[56] References Cited

U.S. PATENT DOCUMENTS

| 951,989 | 3/1910 | Hanger | 623/56 |
|---|---|---|---|
| 1,804,915 | 5/1931 | Collins | 623/56 X |
| 2,126,654 | 8/1938 | Morris | 623/56 X |
| 2,197,093 | 4/1940 | Campbell | 623/56 |
| 4,619,661 | 10/1986 | Axelsson | 623/55 |
| 4,911,724 | 3/1990 | Fikes | 623/56 X |
| 4,959,073 | 9/1990 | Merlette | 623/55 |
| 5,019,109 | 5/1991 | Voisin | 623/55 X |

FOREIGN PATENT DOCUMENTS

| 0022172 | of 1898 | United Kingdom | 623/56 |
|---|---|---|---|
| 8909036 | 10/1989 | World Int. Prop. O. | 623/53 |

*Primary Examiner*—Ronald Frinks
*Assistant Examiner*—D. Willse
*Attorney, Agent, or Firm*—Knobbe, Martens Olson & Bear

[57] ABSTRACT

A prosthetic foot is characterized by the provision of one or more bladders to vary the performance characteristics of the prosthesis. The bladders preferably include multiple chambers formed by full or partial bifurcation of the bladder, and may be tapered to permit operative alignment of the bladder with certain structural members of the foot. The pressure in the bladder is preferably alterable through the provision of valve means communicating with the bladder. A retaining strap is preferably provided to limit the movement of certain structural members of the foot with respect to other such structural members.

9 Claims, 3 Drawing Sheets

PROSTHETIC FOOT INCORPORATING ADJUSTABLE BLADDERS

BACKGROUND OF THE INVENTION

This invention relates to prostheses in general, and specifically to the use of an adjustable bladder in a prosthesis such as a prosthetic foot, which bladder is useful to modify or fine-tune the performance characteristics of the prosthesis. In particular, the bladder may be juxtaposed to various structural members of the prosthesis to "cushion" or otherwise limit or modify the movements thereof.

Although many prosthetic devices have attempted to simulate the ambulation of a normal foot, virtually all of them are not readily adjustable in terms of their performance characteristics. This adjustability is especially desirable among amputees who participate in a variety of physical activities requiring varying levels of energy-storing and -releasing attributes.

Certainly, some prior art devices more nearly achieve the desired ease of adjustability than do others. For example, see my U.S. Pat. No. 4,547,913 for my invention relating to a "Composite Prosthetic Foot and Leg", and U.S. Pat. No. 4,822,363 for my invention relating to a "Modular Composite Prosthetic Foot and Leg". Also, my pending applications Ser. Nos. 07/337,374, 07/585,920 and 07/293,824,now U.S. Pat. No. 5,037,444, disclose prosthetic foot devices with similar preferred materials and methods of manufacture, and with corresponding benefits therefrom.

Each of my aforementioned inventions is characterized by lightweight, elongated structures incorporating polymer impregnation of superimposed reinforcing laminae maintained in the desired configuration. Such configurations and constructions provide the desirable characteristics of strength and flexibility in the prosthetic member, and achieve a simulation of the performance of natural feet which had previously not been attainable. Such prostheses may be provided in modular assemblies, whereby the particular performance characteristics of a given prosthesis may be adapted and readily adjusted to meet the needs and activity level of the individual patient.

Notwithstanding the valuable contribution and characteristics of my aforementioned patents and pending applications and specifically the modularity thereof, the adjustment of those prostheses is relatively involved in comparison to that of the present invention. Any adjustment of the performance characteristics of those prostheses broadly requires the disassembly of a covering shroud (if present) and of structural members from each other (through bolt, nut, and washer combinations, for example). After a new combination of structural members has been selected, it must similarly be reassembled.

Other prosthetic foot devices are even less readily adjusted, and include U.S. Pat. No. 3,335,428 to Gajdos, which attempts to duplicate the skeletal and skin structure of a natural human foot, U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

Moreover, the dynamic performance of most prior art devices is relatively stiff and immediate, and cannot approach the gradual "cushioning" achievable with the use of the bladders of the instant invention in connection with structural members.

Additionally, where bladders have been utilized in prosthetic devices, they have been relatively limited in their performance and usefulness by their configuration. For example, U.S. Pat. No. 708,685 discloses a pneumatic sole 36, FIG. 2, which interacts with pistons 36 (the number 36 was mistakenly used for two different parts in the patent) and 37 and with a section 35 of the sole 36 to mimic flexure and cushioning of a natural foot. In U.S. Pat. No. 1,151,144 to Wofe et al., an air bag 3 (FIG. 4) is filled with air to a desired pressure through a valve 4 (FIG. 2). Both of these patents disclose relatively basic uses of pneumatic devices in prostheses, but include significant shortcomings, such as the apparent likelihood that the wearer may experience a feeling of being "high-centered", especially with respect to lateral stability.

OBJECTS AND ADVANTAGES OF THE INVENTION

It is, therefore, an object of my invention to provide a prosthetic foot incorporating bladders which achieve a more gradual dynamic transition during loading than possible with prior art devices. The foot preferably includes a number of structural members fabricated, for example, from materials and methods similar to those disclosed in my above-listed patents and applications. Such members provide desirable energy-storing and -releasing characteristics and may be readily assembled and configured to receive and interact with bladders of the type hereindescribed.

Another object of my invention is to provide a prosthetic foot of the aforementioned character in which the bladder or bladder members are readily adjustable in pressure, in order to permit a corresponding ready adjustment of the feel and performance of the prosthesis experienced by the wearer.

Moreover, the preferred embodiment of the bladder of my invention may be fabricated in a variety of configurations, including those having multiple chambers and tapered cross-sections. Such configurations permit the bladder or bladders to be positioned in unusual but useful locations within the prosthesis and the structural members thereof, and provide additional benefits such as a lessened feeling of being "high-centered", as described above.

It is a further object of my invention to provide a bladder useful in prosthetic devices such as a prosthetic foot of the aforementioned character. In a preferred embodiment, and as indicated above, the bladder includes means for adjusting the internal pressure and the corresponding feel and performance characteristics of the bladder and the prosthesis into which it is incorporated.

The prosthetic device of the invention, including the structural members and the bladders, is preferably of modular configuration, resulting in ready assembly and adjustability thereof, similar to my aforementioned inventions. The various components of the foot of my invention preferably can be readily exchanged with correspondingly-constructed components, or even differently-constructed components, to provide size and performance adjustments and adjustability to suit the size of foot of the amputee or the stride, height, weight, and activity level of the amputee. Therefore, a range of combinations of spring rate, adjustability and size can be provided to the amputee, achieving a natural stride and resilience of gait, which has not been fully obtainable by prior art prosthetic devices.

Consequently, the foot of my invention is characterized by extreme light weight, instantaneous response to imposed loads and correspondingly instantaneous delivery of stored energy when the gait of the wearer indicates that such stored energy is to be released. The wearer of the foot may engage in a wide variety of activities and may easily and precisely adjust the stiffness and spring characteristics according to the particular activity.

Other objects and advantages of the invention will be apparent from the following specification and the accompanying drawings, which are for the purpose of illustration only.

DESCRIPTION OF PREFERRED EMBODIMENT

Figure 1:
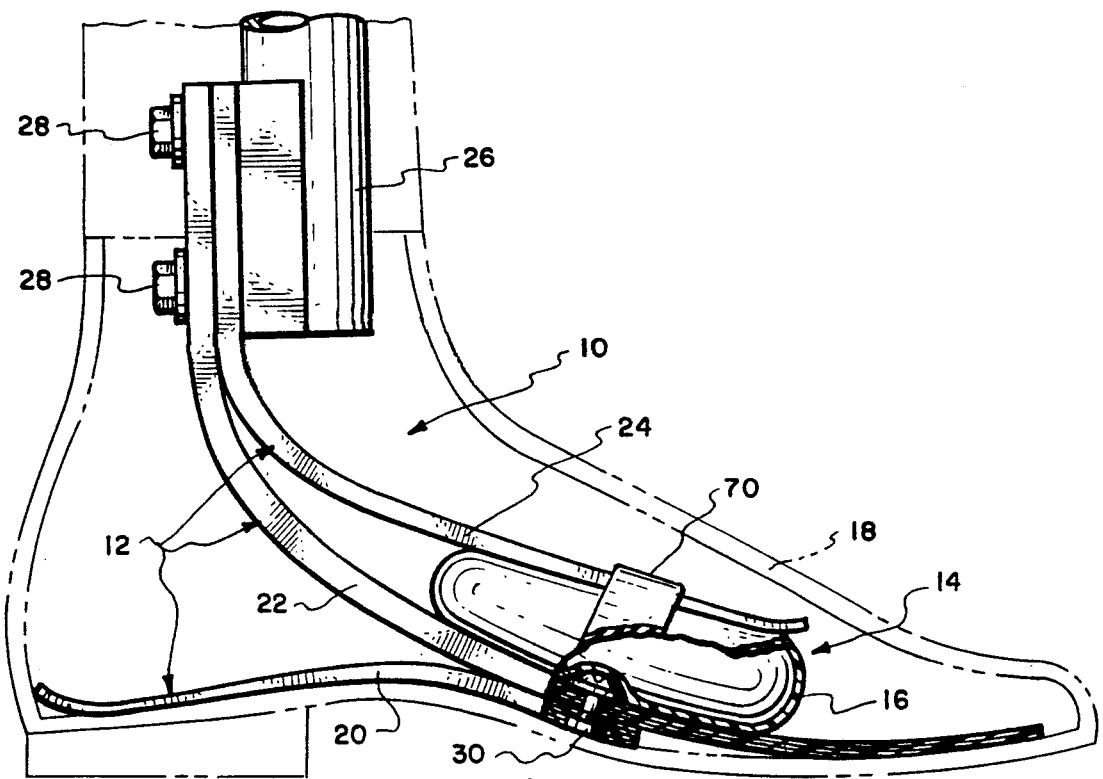
FIG. 1 is a side elevation view of a prosthesis constructed in accordance with the teachings of the invention and incorporating a single bladder member.

Referring to the drawings, and particularly to FIG. 1 thereof, I show a foot prosthesis 10 constructed in accordance with the teachings of the invention and including structural members 12 and bladder means 14 such as a bladder member 16 operably assembled therewith. A shoe 18 is shown in phantom as it might be worn with the prosthesis.

As indicated above, the structural members 12 may be fabricated, combined and assembled in a wide variety of shapes, sizes, and performance characteristics, and are preferably constructed from materials and methods described in my previously mentioned patents and pending applications. For purposes of illustration, FIG. 1 discloses structural members including a heel portion 20, a forefoot portion 22, and an auxiliary member 24.

In the preferred embodiment, the forefoot portion 22 and the auxiliary member 24 are operatively attached to a pylon 26 through the use of nut and bolt combinations 28 or similar expedient, or are otherwise adapted for operative disposition on a wearer's stump. The heel portion 20 is operatively (and preferably demountably) connected to the forefoot portion 22 through the utilization of nut and bolt combinations 30 or the like.

Figure 4:
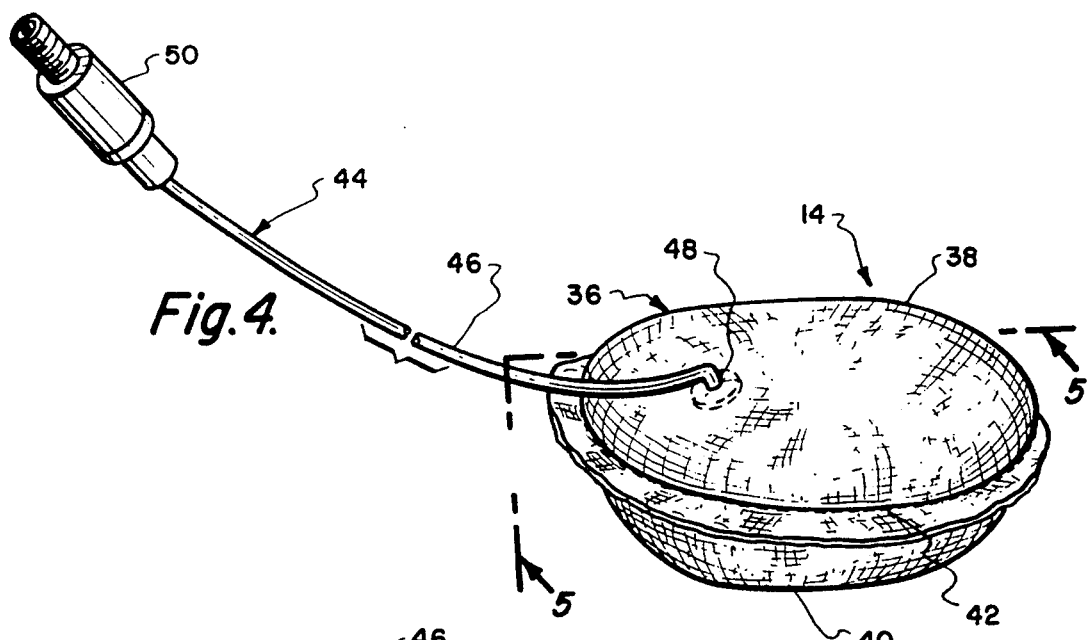
FIG. 4 is an isometric view of an adjustable bladder means constructed in accordance with the teachings of the invention.
Figure 5:
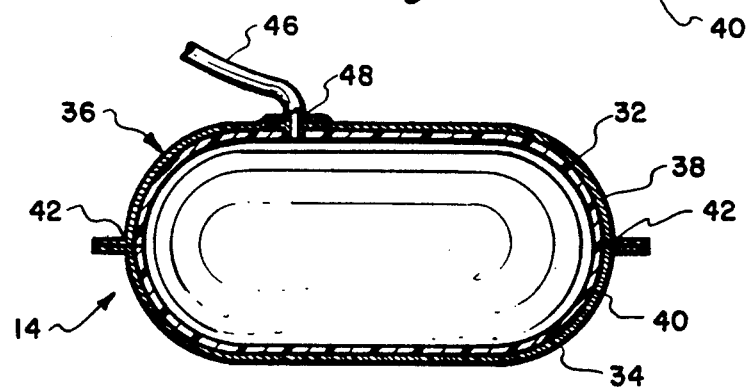
FIG. 5 is a sectional side elevation view, taken along line 5—5 of FIG. 4.

The bladder means 14 such as bladder member 16 is preferably fabricated from a suitably strong, flexible, leak-proof, lightweight material such as urethane or the like. By way of example, FIGS. 4 and 5, the bladder may be formed by heat sealing appropriately sized and shaped pieces of material 32 and 34 to each other. Suitable thicknesses of urethane have been found to be 0.01 to 0.02 inches, but a wide range of thicknesses and materials may be utilized with efficacy. Bladder pressures of up to 80 psi have been utilized with efficacy.

The bladder means 14 is preferably enwrapped in covering means 36 fabricated of Kevlar or similarly strong material to prevent the bladder means 14 from exploding under high pressures and to help define the final inflated shape of the bladder means 14. In preferred embodiments, FIGS. 2, 4–7, covering means 36 includes sections 38 and 40, which may be stitched together (as indicated at 42) at the perimeter of the bladder member 16, before or after the sections 38 and 40 have been cut to their desired final shapes. Those skilled in the art will understand that a variety of covering materials and methods of fabrication and assembly thereof may be utilized with efficacy, without departing from the teachings of my invention.

Bladder means 14 is preferably encloses air, $CO_2$, or a similar gas-like substance, but may alternatively enclose liquids or gels such as water, silicone, or the like. Any such assembly may provide the desired deformability and consequent "cushioning" or energy-storing, absorption and release.

To provide ready adjustment of the spring rate and performance of the prosthesis to the wearer, bladder means 14 preferably includes adjustment means 44 such as a PVC or urethane tube 46 which is solvent-bonded or otherwise suitably attached to the bladder member 16 (such as at 48) so as to be in fluid or gaseous communication with the interior of the bladder.

Adjustment means 44 further preferably includes appropriate valve means 50 on the opposite end of the tubing 46. In the preferred embodiment, the valve 50 is adapted to receive a needle from an air pump (not shown) or from a $CO_2$ cartridge (not shown), as more thoroughly described herein, and may be disposed on a suitable bracket 52, FIGS. 2 and 3, for ready accessibility to the wearer. The valve member may be operatively connected to the tubing 46 by expanding the end of the tubing and inserting the valve therein, as at 54, or through the provision of an adaptor 56.

Figure 2:
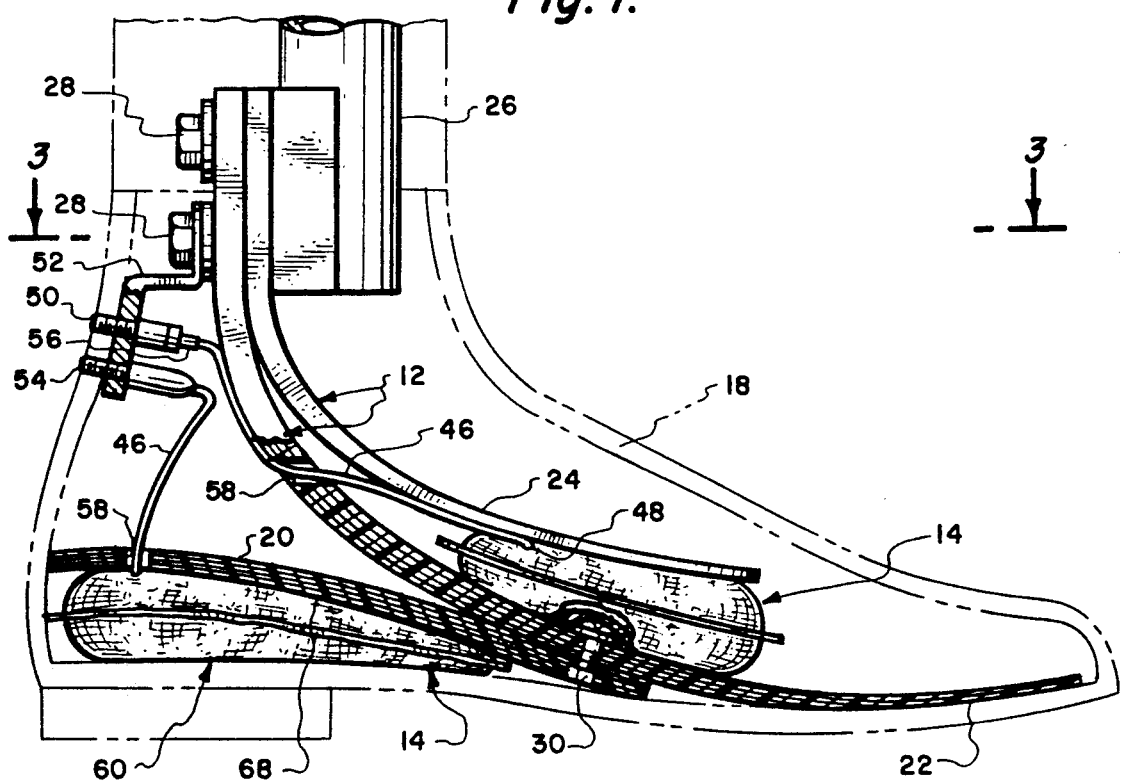
FIG. 2 is a side elevation view of an alternative embodiment of a prosthesis constructed in accordance with the teachings of the invention, and is similar to FIG. 1 but includes an additional bladder member and means for adjustment of the internal pressure of the bladders.
Figure 3:
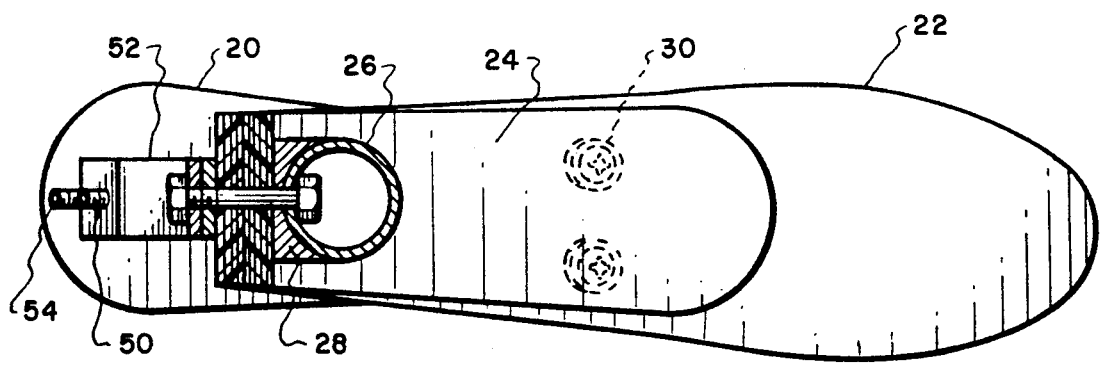
FIG. 3 is a plan view, taken along line 3—3 of FIG. 2.

If indicated, passageways such as holes 58, FIG. 2, may be provided in the structural members 12 to accommodate the tubing 46. The passageways 58 are preferably of a size and are positioned to facilitate assembly and ambulation of the prosthesis without binding or damaging the tubing 46.

Figure 6:
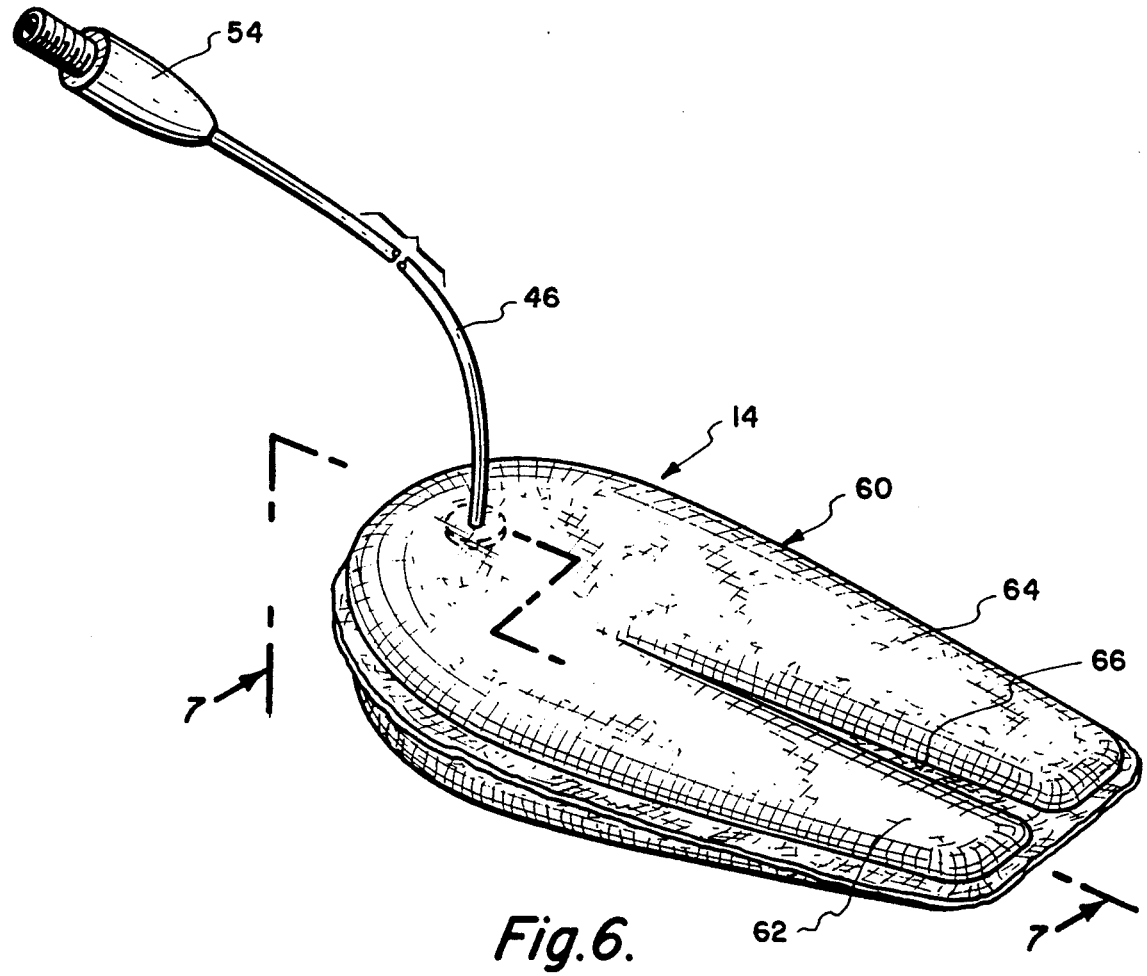
FIG. 6 is an isometric view of an alternative embodiment of an adjustable bladder means constructed in accordance with the teachings of the invention.
Figure 7:
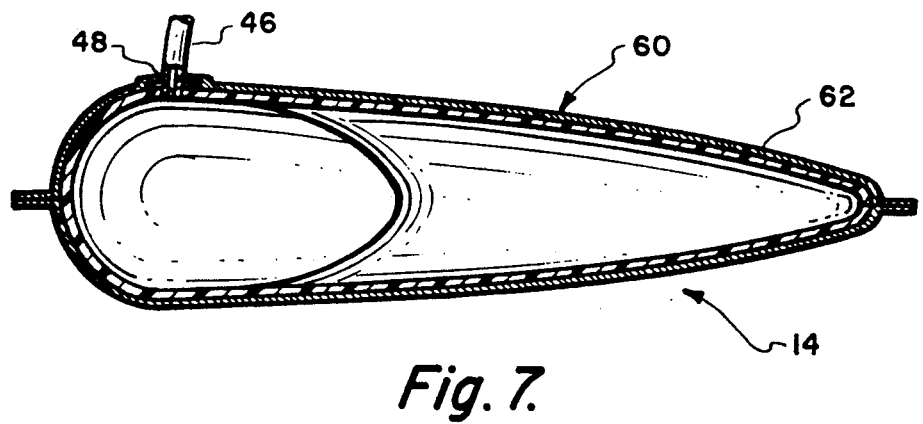
FIG. 7 is a sectional side elevation view, taken along line 7—7 of FIG. 6.

An alternative embodiment 60 of the bladder means 14 is illustrated in FIGS. 6 and 7, and is fabricated and operated in a manner similar to that described above, but is bifurcated or otherwise divided to include chambers 62 and 64. This bifurcation may be readily achieved by heat-sealing a strip 66 across all (not shown) or a portion of the bladder 60, or may be fabricated in numerous other manners. Such constructions may include a wide variety of shapes (such as the modified U-shape of FIG. 6) and any beneficial number of chambers, which chambers may or may not be in gaseous or fluid communication with one another, depending on the desired performance of the bladder.

The provision of the heat-sealed strip 66 in the bladder 60 provides a number of benefits to the wearer of the prosthesis. For example, the strip 66 may be utilized to cause a tapering or reduction in cross-section along the length of the bladder means 14, as best illustrated in FIG. 7. A tapered bladder may be more readily disposed in certain locations in the prosthesis 10 than is a non-tapering bladder, such as under a structural heel member 68, FIG. 2. Such a bladder may also provide more desirable or more gradual cushioning effects than a non-tapering bladder.

Additionally, the provision of multiple chambers such as chambers 62 and 64 reduces and even eliminates the above-described problem of feeling "high-centered". Instead of providing only a central contact location between the bladder member 60 and the overlying heel member 68, FIG. 2, the chambers 62 and 64 provide multiple contact surfaces and dispose such areas of contact laterally from the center of the heel member 68.

Another beneficial modification to my invention is the provision of a restraining or retaining means such as a strap 70, FIG. 1. The strap 70 is fabricated from a suitably tough, flexible material such as impregnated canvas or the like, and is configured and assembled with the structural members 12 and/or the bladder means 14 to achieve desired stress-storage and -release performance in the prosthesis.

For example, the strap 70 may be operatively attached to the forefoot portion 22 through the aforesaid assembly 30 of nuts and bolts, and may be releasably attached around the auxiliary structural member 24 through the provision of Velcro®-type fasteners or similar expedient.

The strap 70 provides a number of benefits. For example, if juxtaposed to a bladder member 16, the strap may be appropriately tightened to "flatten" the bladder, thus increasing the contact areas between the structural members and the bladder, and possibly reducing the "high-centered" problem discussed above.

Moreover, restraining means such as the strap 70 may be incorporated at various locations on the prosthesis 10 to restrict the distance that associated structural members 12 may move from one another. The retaining means may be utilized to prevent undesirable excessive loading and stressing of a particular member 12, and to combine the spring-stress response characteristics of the associated structural members 12 under certain loading conditions. For example, the strap 70 as assembled in FIG. 1 permits the auxiliary member 24 to assist in raising the toe of the prosthesis 10 and to store and release spring energy when the heel portion 20 is struck on the ground in front of the wearer.

In operation, the bladders may be completely deflated if the wearer desires the performance characteristics of the structural members. For example, in the assembly illustrated in FIG. 3, the forward bladder means 14 would be non-functional if deflated, and the spring-stress response of the auxiliary member 24 would be combined with that of the forefoot portion 22 only after the forefoot portion was sufficiently deflected to contact the auxiliary member 24.

As the bladder is inflated to increasing pressures and volumes, however, the combination of the spring-stress responses of the forefoot portion 22 and the auxiliary member 24 effectively occurs after correspondingly less and less deflection of the forefoot portion. If the bladder member is sufficiently inflated, the forefoot portion 22 and the auxiliary member 24 would *always* act and react in unison.

Additionally, the above-indicated cushioning effect of the bladder means 14 can be dependent upon the degree to which the bladder is inflated. Although the bladder will preferably always retain some amount of compressibility and "cushioning", the compressibility could approach a negligible amount if the bladder is sufficiently inflated, thereby virtually eliminating any cushioning effect during ambulation of the prosthesis 10.

Those skilled in the art will understand that the bladder means of my invention may be utilized with efficacy in a wide variety of prosthetic devices, including prosthetic feet of substantially different configurations than those disclosed in the drawings.

It will be obvious to those skilled in the art that an extremely wide variety of performance characteristics may be achieved through the incorporation of the bladder means of my invention into any given assembly of structural prosthetic members. Moreover, the selection of and adjustment to a desired set of performance characteristics may be readily achieved by the wearer of the prosthesis without the need for disassembly and reassembly of various components. The wearer may repeatedly adjust the spring-stress response characteristics of the foot with very little time or effort required. The valve means 50 includes a bleed function to release pressure in the bladder and, as explained above, permits ready inflation of the bladder through the use of a hand pump, a $CO_2$ cartridge or the like.

For example, if an individual partakes in sports or other activities which subject the prosthesis 10 to greater loads than those of normal daily wear, the bladder members 16 may be appropriately inflated prior to the periods of greater activity, and deflated thereafter.

The prosthesis and bladder means of my invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

I claim:

1. In a prosthetic foot, the combination of: attachment means to facilitate operative engagement of the foot with a wearer's stump; a plurality of elongated, non-inflatable, curvilinear structural members operatively attached to said attachment means and/or to each other, said structural members providing substantial energy storage and return during ambulation; and bladder means adjacent said structural members, whereby said bladder means cooperate with said structural members in determining the energy-storage characteristics of said foot, said foot constituting means for substantially operable ambulation without regard to the presence or pressure of said bladder means.

2. The prosthetic foot of claim 1, in which at least one of said bladder means is provided with a plurality of chambers.

3. The prosthetic foot of claim 1, in which at least one of said bladder means is formed in a modified U-shaped configuration.

4. The prosthetic foot of claim 1, in which at least one of said bladder means includes a partial bifurcation which divides said bladder means into a plurality of sections while retaining fluid communication between said sections.

5. The prosthetic foot of claim 1, in which said bladder means includes a heel bladder operatively disposed beneath a lower, rearwardly disposed structural member.

6. The prosthetic foot of claim 1, in which said bladder means is covered with a protective material.

7. The prosthetic foot of claim 1 or claim 2 or claim 3 or claim 4 or claim 5 or claim 6, including retaining means juxtaposed to a plurality of said structural members to restrict the movement of said members in relation to one another.

8. The prosthetic foot of claim 1 or claim 2 or claim 3 or claim 4 or claim 5 or claim 6, including adjustment means operatively associated with said bladder means to facilitate adjustment of the pressure or volume of said bladder means.

9. The prosthetic foot of claim 1 or claim 2 or claim 3 or claim 4 or claim 5 or claim 6, in which said bladder means contains a gaseous substance.

* * * * *